United States Patent [19]

Kitamura et al.

[11] Patent Number: 5,423,216

[45] Date of Patent: Jun. 13, 1995

[54] APPARATUS FOR AUTOMATICALLY DETERMINING BULK SPECIFIC GRAVITY OF POWDERY PRODUCT

[75] Inventors: Hajime Kitamura, Ichihara; Masaru Takeuchi; Hideo Yoshikoshi, both of Hasaki; Mikio Kitai, Mito; Takashi Chino, Iruma; Yuji Nogami, Kawaguchi; Hajime Yashiro, Sagara; Keisuke Kato, Kawasaki, all of Japan

[73] Assignee: Shin-Etsu Chemical Co., Ltd., Japan

[21] Appl. No.: 167,033

[22] Filed: Dec. 16, 1993

[30] Foreign Application Priority Data

Dec. 24, 1992 [JP] Japan .................................. 4-344768
Dec. 24, 1992 [JP] Japan .................................. 4-344769

[51] Int. Cl.6 .............................................. G01N 9/02
[52] U.S. Cl. .................................... 73/433; 73/434; 73/435; 73/436; 364/558; 364/567
[58] Field of Search ................... 73/433, 435, 436; 364/558, 567

[56] References Cited

U.S. PATENT DOCUMENTS 3,619,719  11/1971  Waller et al. ..................... 317/2 F
4,843,579  6/1989  Andrews et al. ................... 364/567
5,340,262  8/1994  Tsujimoto et al. ................. 414/273

FOREIGN PATENT DOCUMENTS 0053640  3/1982  Japan ................................. 73/433

*Primary Examiner*—Richard E. Chilcot, Jr.
*Assistant Examiner*—Max H. Noori
*Attorney, Agent, or Firm*—Parkhurst, Wendel & Rossi

[57] ABSTRACT

An apparatus which permits continuous automatic determination of the bulk specific gravity of a powdery sample and highly precise measurement thereof. The apparatus comprises a robot 3 transporting a container 2 filled with a powdery sample; a funnel 4 provided with a damper, which receives the powdery sample discharged from the container 2; a damper-driving unit 5a for pulling out and pushing the damper 5; a sample sensor 7 for detecting the powdery sample dropped through the funnel 4 provided with a damper; a constant volume receiver 6 for receiving dropped through the funnel 4 provided with a damper; a scraping bar 8 for sliding the upper face of the constant volume receiver 6; a scraping bar-driving unit 8a for reciprocating the scraping bar 8; a constant volume receiver-conveying robot 21 transporting the constant volume receiver 6; an electronic balance 22 which determines the weight the powdery sample in the constant volume receiver 6; and a cleaner 23 for aspirating the weighed powdery sample.

6 Claims, 12 Drawing Sheets

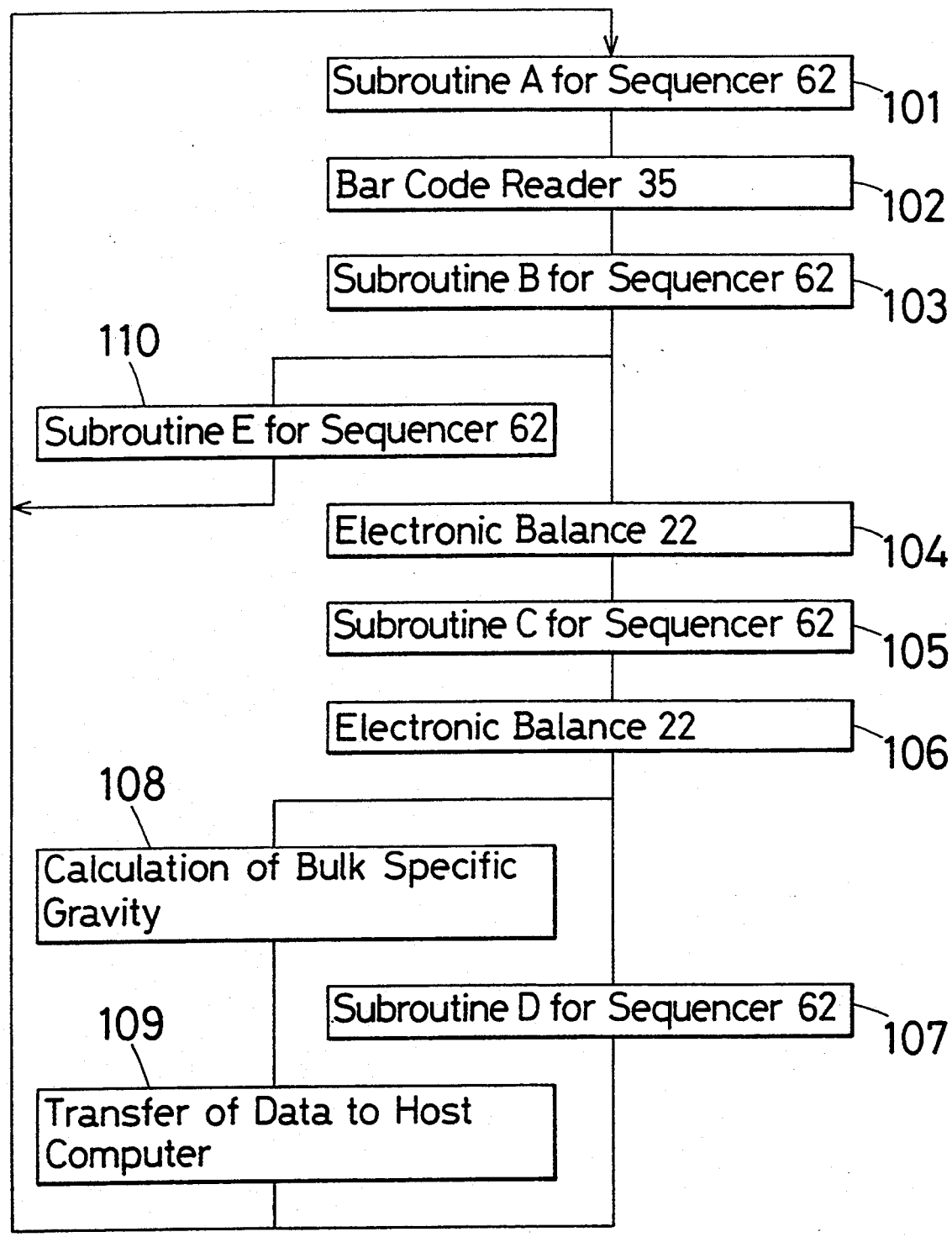

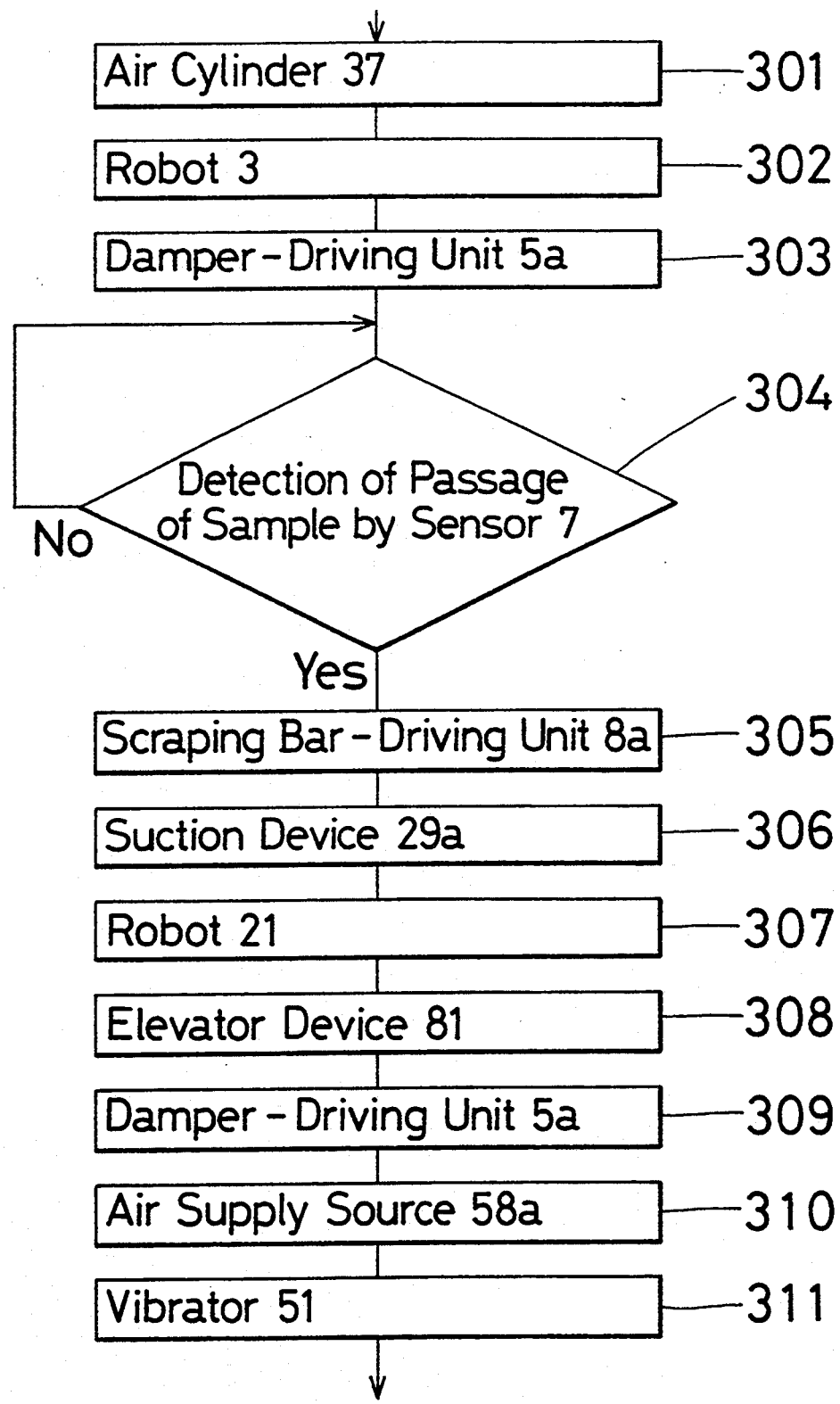

Subroutine C

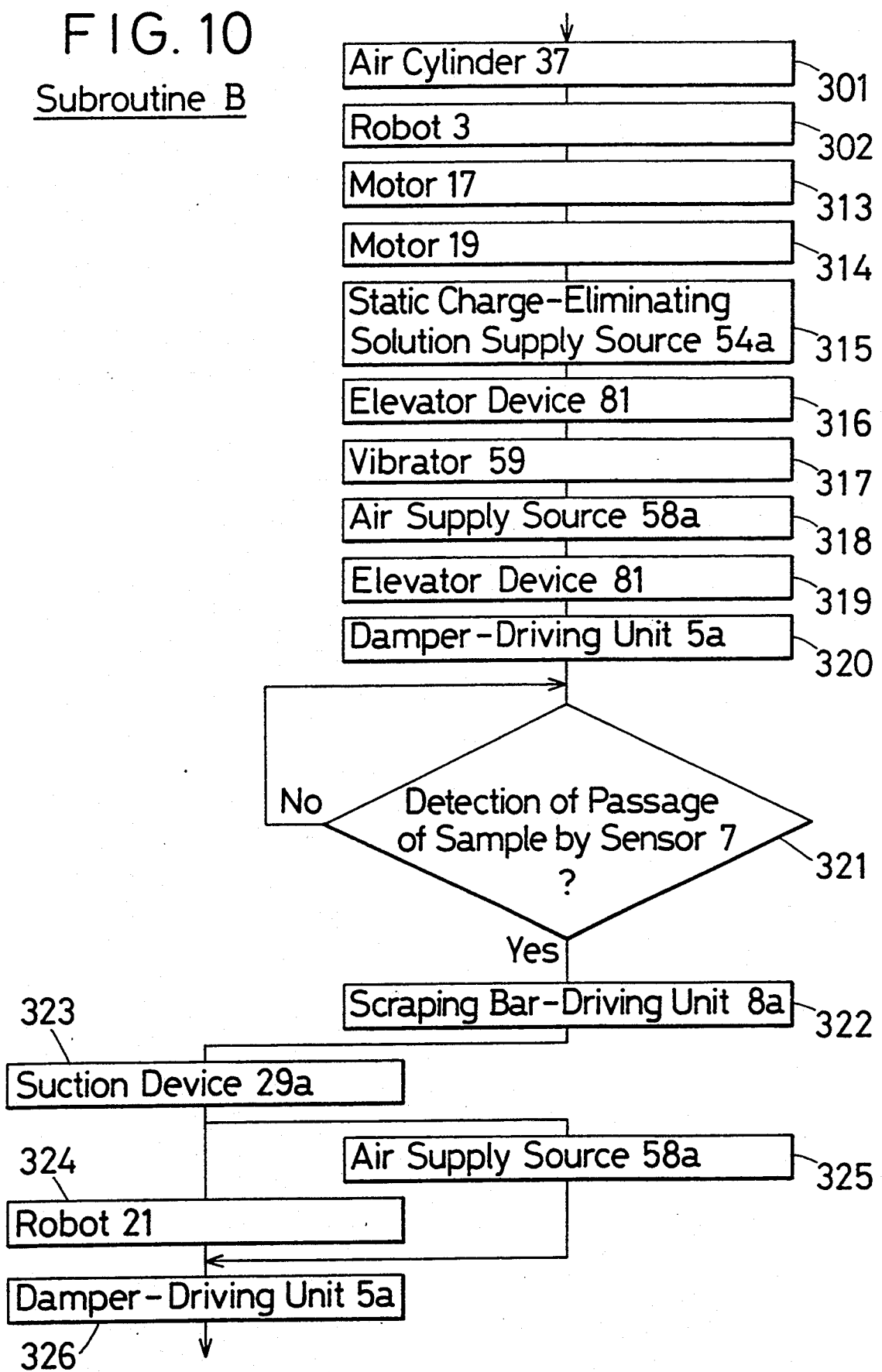

APPARATUS FOR AUTOMATICALLY DETERMINING BULK SPECIFIC GRAVITY OF POWDERY PRODUCT

BACKGROUND OF THE INVENTION

The present invention relates to an apparatus for automatically determining bulk specific gravities of powdery products such as resin powder of, for instance, vinyl chloride resins, ABS resins and MBS resins; powder of foods and cement.

When preparing resin powder or forwarding the powdery product from a manufacturing plant, the product is in general subjected to analysis or quality inspection for various predetermined properties. The results thus obtained are sent back to the manufacturing plant for the improvement of production processes or they are used in the denotation of the quality in order to afford convenience to the destination or the consignee.

In case of, for instance, vinyl chloride resin powder, one of the items for quality inspection thereof is to determine the bulk specific gravity. The determination of bulk specific gravity is in general performed using a funnel provided with a damper and a cylindrical receiver as defined by JIS-K-6721. According to JIS-K-6721, a powdery sample sufficiently admixed is introduced into the funnel and immediately thereafter, the damper is pulled out so that the powdery sample drops into the receiver. After the excess powdery sample is scraped off, by a glass bar, from the receiver which is heaped with the powdery sample, the weight of the receiver filled with the powdery sample (the gross weight) is determined accurately. The weight of the receiver per se (the tare weight) is subtracted from the gross weight to give the true weight of the powdery sample (the net weight) and then the net weight of the sample is divided by the inner volume of the receiver to thus obtain the bulk specific gravity of the sample.

Reproducible results cannot always be obtained even if a specific powdery sample is inspected for the bulk specific gravity several times, while faithfully following the regulation defined by JIS-K-6721. In particular, the measured values for a particular powdery sample widely vary depending on operators. The inventors of this invention have conducted various investigations on this point and have found out that such scattering in the measured values is caused due to subtle differences in the manner of measuring operations for every measurement. In particular, the manner of operations significantly vary depending on operators and this results in the scattering in measured values. For instance, the packing density of a powdery sample observed when the sample is quickly introduced into the funnel substantially differs from that observed when it is gently introduced into the funnel. This is delicately reflected in the velocity of the powdery sample dropped through the funnel and in turn in the packing density of the powdery sample in the receiver.

In addition, the density of the powdery sample in the receiver is influenced by the difference in the speeds of the damper pulled out from the funnel and the contact between the damper and the powdery sample filled to the brim upon dropping the sample into the receiver and the removal of the heaped-up powdery sample by scraping it off with the glass bar. Moreover, it has also been elucidated that the charging of the powdery resin sample during, for instance, transmission through a piping and any change in the environment for measurement greatly affect the measured values of the bulk specific gravity thereof. For instance, the humidity in the environment enclosing the measuring system is greatly influenced by the weather change and this is reflected in the rate of electrification of the resin powder and hence the packing density of the powdery sample in the receiver. Accordingly, reproducible results cannot be obtained.

Furthermore, in the conventional apparatus for determining the bulk specific gravity, such operations must be manually carried out. Therefore, the conventional apparatus requires much labor and time and correspondingly the efficiency thereof becomes low. In particular, the receiver filled with the powdery sample should be handled with the greatest circumspection. Besides, the receiver must be completely cleaned after each measurement is completed to ensure the precision of the measurement subsequently performed. This makes the measurement quite troublesome.

SUMMARY OF THE INVENTION

Accordingly, an object of the present invention is to provide an apparatus for automatically determining a bulk specific gravity of powdery product which allows continuous automatic determination of the bulk specific gravity of a powdery product while eliminating manual operations as much as possible and which can ensure highly precise measurement.

The foregoing object of the present invention can effectively be accomplished by providing an apparatus for automatically determining the bulk specific gravity of a powdery product which comprises, as shown in the attached FIG. 1, a sample container-conveying robot 3 which can hold and transport a sample container 2 filled with a powdery sample and turn the sample container 2 upside down at a position having a predetermined height to discharge the content thereof; a funnel 4 provided with a damper, which receives the powdery sample discharged from the sample container 2; a damper-driving unit 5a for pulling out and inserting the damper 5; a sample sensor 7 for detecting the sample dropped through the funnel 4 provided with a damper; a constant volume receiver 6 for receiving the powdery sample 1 dropped through the funnel 4 equipped with a damper; a scraping bar 8 which can slide on the upper face of the constant volume receiver 6; a scraping bar-driving unit 8a for reciprocating the scraping bar 8; a constant volume receiver 6-conveying robot 21 which can hold and transport the constant volume receiver 6 filled with the powdery sample 1 and which can turn the receiver 6 upside down; an electronic balance 22 which receives the constant volume receiver 6 transferred thereto by the robot 21 and determines the weight thereof; and a cleaner 23 for cleaning the sample container by aspirating the weighed powdery sample. Moreover, the apparatus comprises, as shown in FIG. 5, control circuits 61 and 62 for controlling the operations of the sample container-conveying robot 3, the damper-driving unit 5a, the scraping bar-driving unit 8a, the constant volume receiver-conveying robot 21, the electronic balance 22 and the cleaner 23.

In the apparatus for automatically inspecting a powdery product for the bulk specific gravity thereof, the sample container-conveying robot 3 holds the sample container 2, transports the container 2 to a predetermined position above the funnel 4 provided with a damper and turns the container upside down so as to discharge the powdery sample 1 present therein to the funnel 4, in accordance with the instructions inputted thereto through the control circuit 62. At this stage, the powdery sample 1 in the funnel 4 is dropped into the constant volume receiver 6 so that the receiver 6 is heaped with the sample when the damper 5 is opened by the action of the damper-driving unit 5a which is put in operation through the instructions outputted from the control circuit 62. After the powdery sample sensor 7 confirms whether the powdery sample 1 is completely dropped from the funnel 4, the scraping bar-driving unit 8a is put in operation in accordance with the instruction outputted from the control circuit 62 and thus the scraping bar 8 slides along the upper face of the constant volume receiver 6 to remove the excess of the powdery sample 1 so that a predetermined volume of the powdery sample remain in the receiver 6. Then the constant volume receiver-conveying robot 21 is put in operation through the instructions outputted from the control circuit 62 so that the constant volume receiver 6 containing the predetermined volume of the powdery sample 1 is transferred to the electronic balance 22 to determine the weight (the gross weight) of the receiver 6 containing the sample 1. The weighed value (the weight of the constant volume of the powdery sample 1 including the tare weight) is transferred from the electronic balance 22 to the control circuit 62. Then the constant volume receiver 6 is transported to the cleaner 23 by the action of the constant volume receiver-conveying robot 21 under the control through the control unit 62 and turned upside down to dispose the weighed powdery sample. The powdery sample remaining in the receiver 6 is aspirated by the cleaner 23 to clean the receiver 6. After completion of the cleaning operation, the vacant constant volume receiver 6 is returned to the electronic balance 22 by the action of the receiver-conveying robot 21 and the weight thereof is determined by the electronic balance 22. The weighed value (the tare weight of the constant volume receiver 6) is transferred to the control circuit 61. Then the receiver 6 is transferred to the predetermined position (home position) immediately below the funnel 4 equipped with a damper through the action of the receiver-conveying robot 21 under the control through the control circuit. The control circuit 61 calculates the bulk specific gravity of the powdery sample on the basis of the weighed values, i.e., the weight of the constant volume of the powdery sample including the tare weight and the tare weight of the receiver 6 which are transferred to the control circuit 61 as well as the volume of the receiver 6 which has been preliminarily stored in the control circuit.

It is also an object of the present invention to provide an apparatus, equipped with a static charge eliminator, for automatically determining the bulk specific gravity of a powdery product which allows continuous automatic determination of the bulk specific gravity while eliminating any influence of electrostatic charges present on the powdery sample on the data obtained and eliminating manual operations as much as possible.

The foregoing object of the present invention can effectively be accomplished by providing another apparatus for automatically determining the bulk specific gravity of a powdery product. As shown in FIG. 3, the apparatus according to this embodiment comprises, in addition to the components shown in FIG. 1, a static charge eliminator 10 which receives and accommodates the powdery sample discharged from the container by the action of the sample container-conveying robot 3 and in which the powdery sample is admixed with a solution for neutralizing or eliminating static charge generated on the sample; and driving units 17 and 19 for the static charge eliminator 10, with the funnel 4 equipped with a damper being arranged at a position such that the funnel 4 can receive the powdery sample discharged from the eliminator 10.

The static charge eliminator 10 preferably comprises a funnel 20 provided with a bottom cover 14 capable of being opened and closed, which is connected to a rotational driving unit 17; a screw agitator 25 inserted in the funnel 20; and a tube 54 the tip of which is inserted in the funnel 20 and which is communicated with a supply source 54a of static charge-eliminating solution. Preferably, the inclined inner wall of the funnel 20 is approximately parallel to the rotational axis of the screw agitator 25 and the funnel 20 is rotated in the direction opposite to the revolutionary direction of the screw agitator 25.

According to a further embodiment of the present invention, the apparatus for automatically determining the bulk specific gravity of a powdery product comprises, in addition to the aforementioned components, a bar code reader 35 for reading a bar code 2a which is adhered to the sample container 2 containing the powdery sample and which stores the coded lot number of the sample and/or conditions for inspection. In this embodiment, the lot number of the sample and the conditions for inspection read by the bar code reader 35 as well as the weighed value determined by the electronic balance 22 are stored in and outputted from the control circuits 61 and 62.

The control circuits 61 and 62 are connected to a host computer as shown in FIG. 5 and the apparatus may be designed in such a manner that the weighed values outputted from the control circuits 61 and 62 can be transferred to the host computer together with the sample lot number and/or the conditions for inspection. In the apparatus for automatically determining the bulk specific gravity of a powdery sample having such a structure, the bar code reader 35 reads and stores, in accordance with the instructions outputted from the control circuit 61, the bar code 2a which is adhered to the sample container 2 and which stores the coded sample lot number and/or the coded conditions for inspection. After the bulk specific gravity is determined, the calculated bulk specific gravity is then put in secondary use together with the sample lot number and/or the conditions for inspection. For instance, they are subjected to display, printing out or data-transfer.

As shown in FIG. 1, the apparatus preferably comprises a conveying device 30 for transporting the sample container 2 containing the powdery sample to a position where the sample container-conveying robot 3 holds the sample container 2.

Moreover, the apparatus preferably comprises, as shown in FIG. 4, a knocker 51b which comes in contact with the outer surface of the funnel 4 provided with a damper and a vibrating bar 51a which is inserted into the funnel 4 provided with a damper down to a position near a discharge port thereof, the knocker 51b and the vibrating bar 51a being connected to a vibrational driving unit 51.

BRIEF DESCRIPTION OF THE DRAWINGS

FIG. 6 is a program chart for use in an arithmetic and control unit comprising the control block circuit shown in FIG. 5;

FIG. 7A, 7B and 7C are control program charts for use in a sequencer for the control block circuit shown in FIG. 5 and each serves as a subroutine for the program shown in FIG. 6;

FIG. 10 is a control program chart for use in a sequencer for the control block circuit shown in FIG. 9.

DETAILED EXPLANATION OF THE INVENTION

Embodiments of the apparatus according to the present invention will hereunder be described in more detail with reference to the accompanying drawings, but the present invention is by no means limited to these specific embodiments.

FIGS. 1, 2, 3 and 4 are an elevational view and a plan view of an embodiment of the apparatus for automatically determining the bulk specific gravity of a powdery product and an elevational view and a perspective view of the principal parts of the embodiment of the apparatus.

Figure 1:
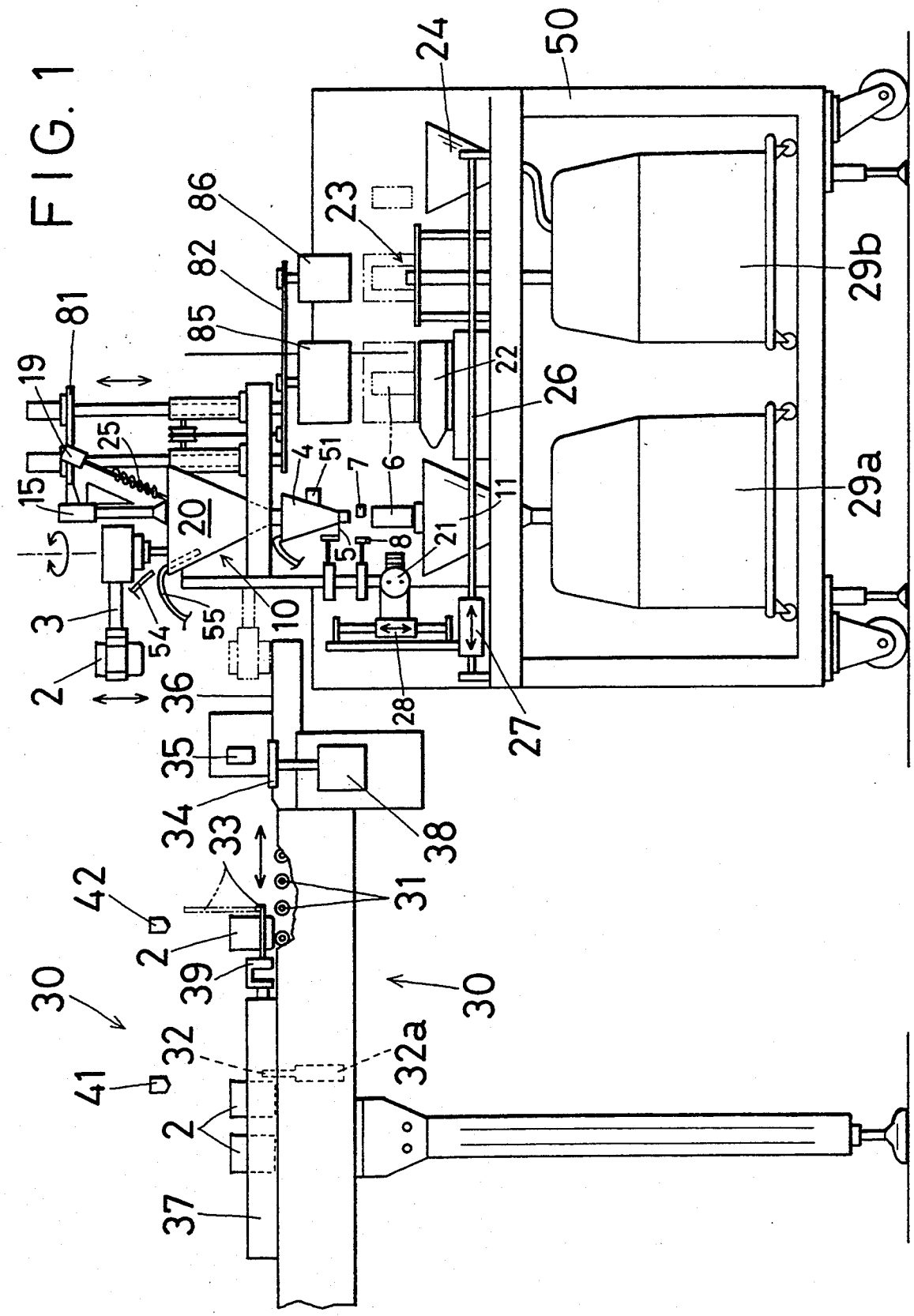
FIG. 1 is a general elevational view showing an embodiment of the apparatus for automatically determining the bulk specific gravity of a powdery sample according to the present invention.
Figure 2:
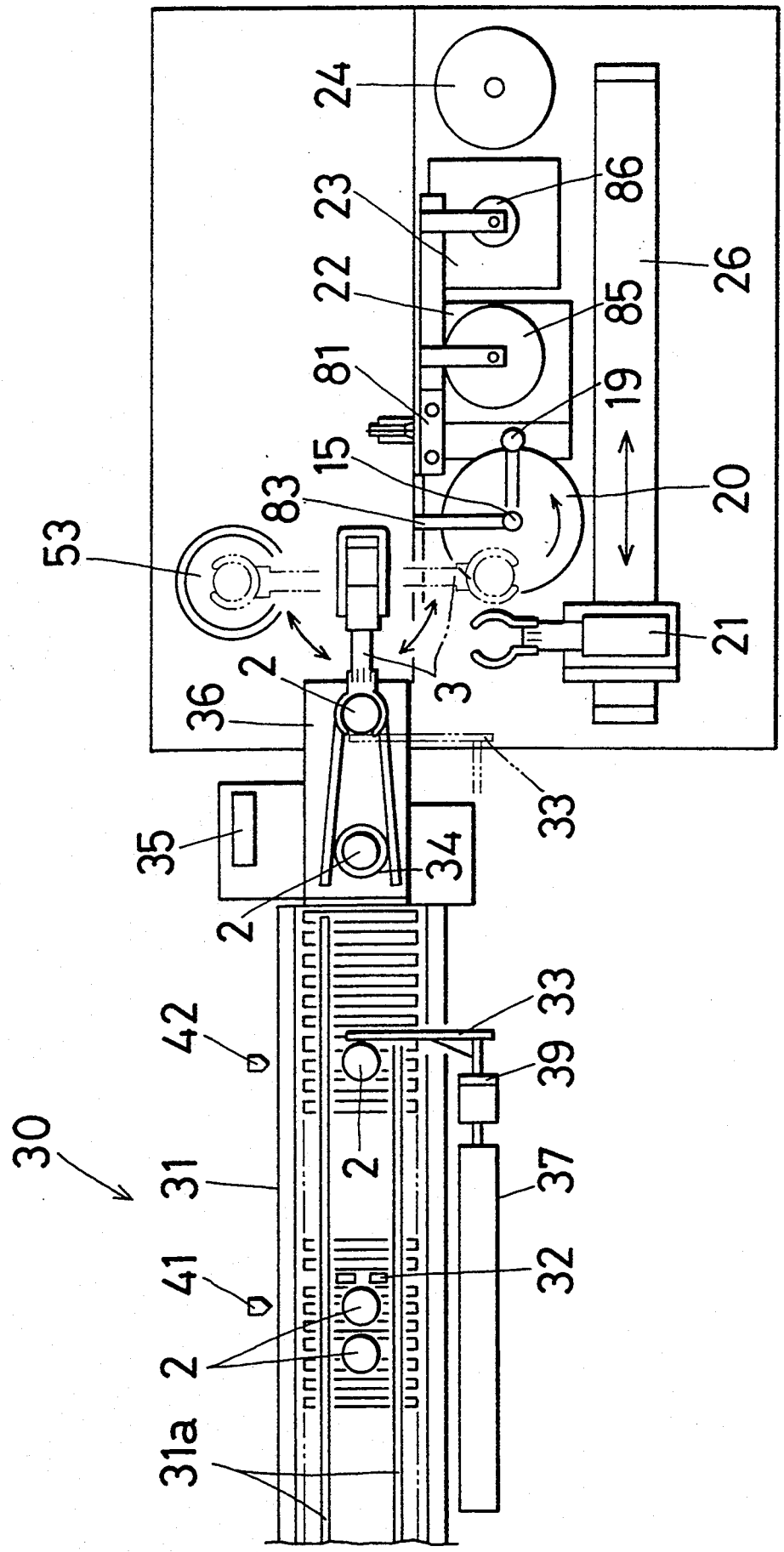
FIG. 2 is a plan view of the embodiment of the apparatus for automatically determining the bulk specific gravity of a powdery sample shown in FIG. 1.

As shown in FIGS. 1 and 2, there are arranged, in order, a roller conveyor 31 of a conveying device 30 for conveying a sample container 2, a bar code reader 35 and a conveyor table 36. The sample container 2 include a powdery resin 1 in an amount of greater than that required for the determination of the bulk specific gravity of the powdery resin and carries, on the outer surface, a bar code 2a comprising coded conditions for inspection inclusive of the name of the powdery resin 1, the lot number and items to be inspected.

Guide rails 31a are provided on the roller conveyor 31 along its conveying direction, which serve as a passage for the sample container 2. A rod-like stopper 32, which is upwardly projected or downwardly retroceded between the rollers of the roller conveyor 31 in response to the reciprocating motion of an actuator 32a, is positioned in the course of the passage and a container sensor 41 for detecting the presence of the sample container 2 is arranged in the proximity to the stopper 32 and on the container-receiver side of the roller conveyor 31. An air cylinder 37 is placed on the side of the roller conveyor 31 so that the cylinder 37 can perform reciprocating motion parallel to the conveying path of the roller conveyor 31. A conveying bar 33 is fitted to the tip of the movable part of the cylinder through a rotary actuator 39. The conveying bar 33 can move from a position above the roller conveyor 31 to a position above the conveyor table 36 by the reciprocating motion of the air cylinder 37 and can likewise vibrate so as to cross the conveying path of the roller conveyor 31 through the action of the rotary actuator 39. The conveying bar 33 has the home position which is a point existing between the stopper 32 and the end of the roller conveyor 31 and a container sensor 42 for detecting the presence of the sample container 2 is arranged in the vicinity of the conveying bar 33 and on the container-receiving side of the roller conveyor 31.

The bar code reader 35 is fitted to the side of a turn table 34 positioned at the end of the roller conveyor 31. The turn table 34 is a disk-like and is connected to a gear motor 38. A flat plane in the proximity to the turn table 34 serves as a transfer table 36 for transporting the sample container 2 whose bar code has been read by the bar code reader 35 to the subsequent step.

Figure 8:
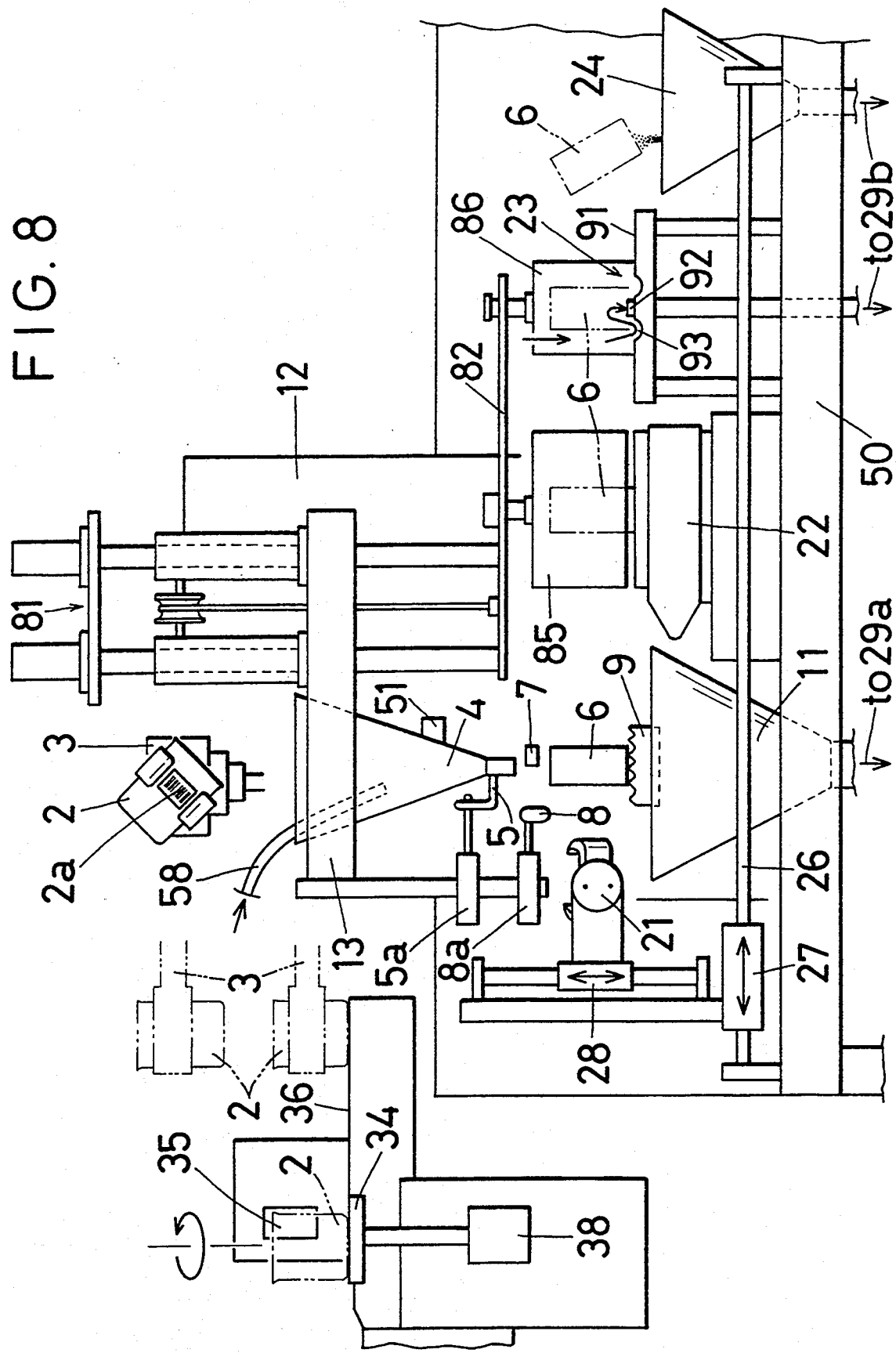
FIG. 8 is an elevational view showing principal parts of another embodiment of the apparatus for automatically determining the bulk specific gravity of a powdery sample according to the present invention.

As seen from FIG. 8, a constant volume receiver 6 is positioned behind a funnel 4 provided with a damper. A sample container-conveying robot 3 is placed above the receiver 6 and the funnel 4. The container-conveying robot 3 holds the sample container 2 and the robot 3 can move up and down, can perform rotational motion (see FIG. 2) and can be turned upside down as shown by two-dot chain lines.

Figure 4:
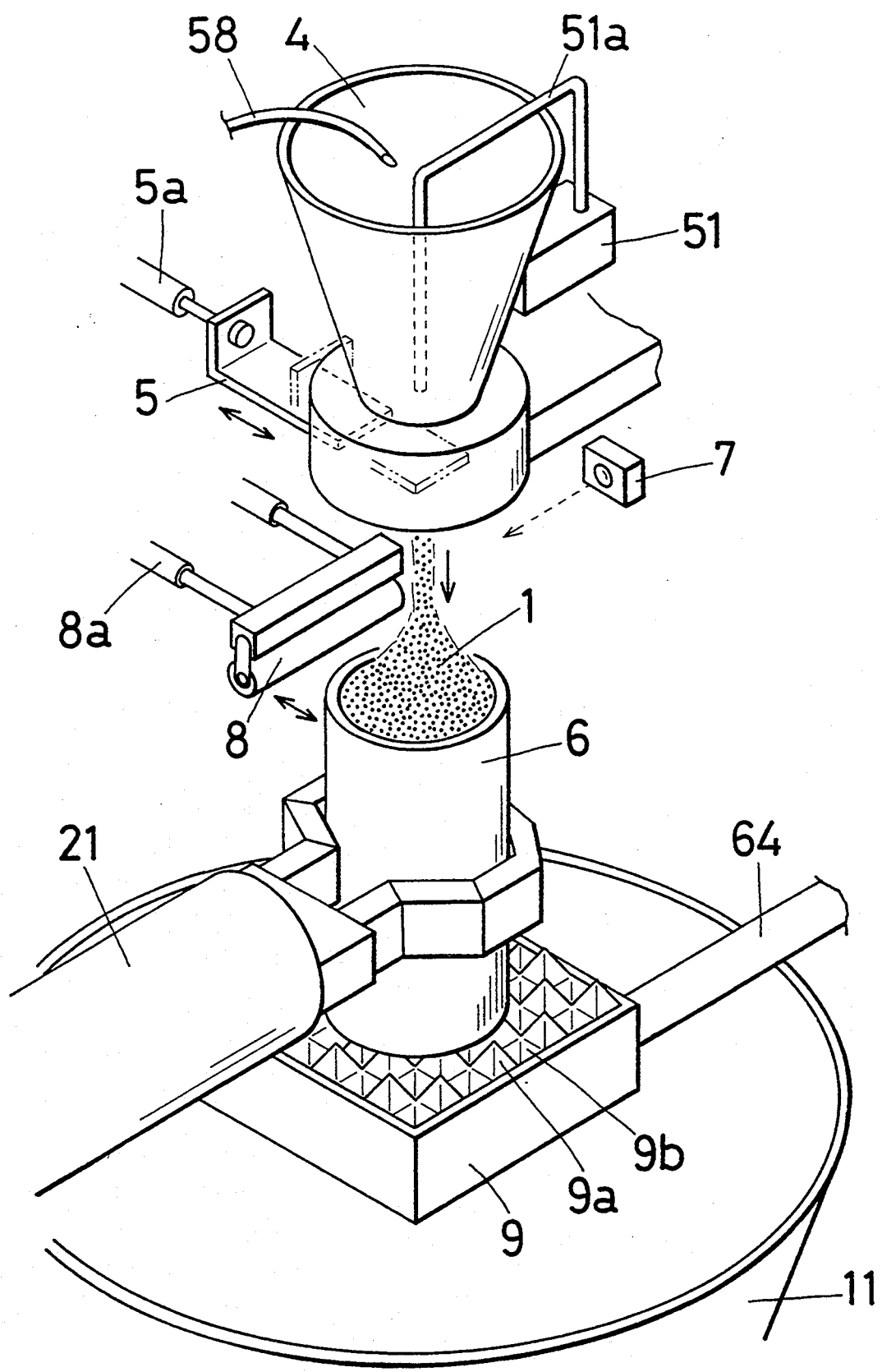
FIG. 4 is an enlarged perspective view showing the principal parts of the embodiment of the apparatus for automatically determining the bulk specific gravity of a powdery sample shown in FIG. 1.

The funnel 4 provided with a damper is one which is geometrically similar with the funnel defined by JIS-K-6721 or whose upper opening is elongated and enlarged along the outer surface of the funnel body defined by JIS-K-6721. The funnel 4 is supported by a support member 13 horizontally projecting from a support plate 12 which is vertically disposed on a base 50. As shown in FIG. 4, a vibrator 51 as a source of vibrational force is fitted to the back face of the funnel 4, a U-shaped vibrating bar 51a is inserted into the funnel 4 and extends from the vibrator 51 to a position in the proximity to the discharge port of the funnel 4 and a knocker 51b comes in close contact with the outer face of the funnel 4 provided with a damper. Moreover, an air tube 58 is introduced into the funnel 4 and is connected to an air-supply source 58a (see FIG. 5). The damper 5 is connected to an electromagnetic damper-driving unit 5a which can undergo horizontal reciprocating motion.

The constant volume container 6 is placed on a pedestal 9 fitted to the support plate 12 through a support member 64. The constant volume receiver 6 is a cylindrical container having an inner volume of 100 cc as defined in JIS-K-6721. A plurality of projections 9a are formed on the upper surface of the pedestal 9 and through holes 9b are formed between these projections 9a. The constant volume receiver 6 is mounted on the pedestal 9 through point contact between the bottom face of the receiver 6 and the tips of the projections 9a. A hopper 11 for receiving an excess of the powdery sample is arranged below the pedestal 9 and is connected to a suction device 29a.

A powdery sample-detecting sensor 7 and a scraping bar 8 are arranged between the funnel 4 and the constant volume receiver 6. The powdery sample-detecting sensor 7 is an optoelectronic sensor which emits a light beam directed towards a position immediately below the funnel 4 and detects the light beam reflected by the powdery sample 1 discharged through the funnel 4. The scraping bar 8 is connected to an electromagnetic scraping bar-driving unit 8a which can perform horizontal reciprocating motion and can slide on the upper face of the constant volume receiver 6. The hopper 11 for receiving the excess of the powdery sample is positioned below the pedestal 9 and connected to the suction device 29a. In addition, a container-disposing opening 53 is formed on the back face of the support plate 12 and serves to dispose the vacant sample container 2 (see FIG. 2).

An electronic balance 22, a cleaner 23 and a hopper 24 for disposing the powdery sample are arranged, in order, along the conveying path of a constant volume receiver-conveying robot 21 mounted on the base 50.

The constant volume receiver-conveying robot 21 comprises an elevator device 28 and an arm for holding the constant volume receiver 6, which is fitted to the elevator device 28. The elevator device 28 is mounted on a table 27 which moves along horizontal rails 26. The constant volume receiver-conveying robot 21 is designed such that it can hold the constant volume receiver 6, can move up and down, can perform horizontal reciprocating motion and can be turned upside down. The robot 21 has a home position (the position shown in FIG. 4) which faces the pedestal 9. The robot 21 is in the stand-by condition at this position where it can hold the constant volume receiver 6.

The electronic balance 22 is one for general use and positioned in such a manner that the level of the upper surface of a weighing table thereof is in agreement with that of the tips of the projections 9a formed on the pedestal 9. A transparent windbreak cover 85 for covering the weighing table is arranged above the electronic balance 22. The windbreak cover 85 is fitted to a crossarm 82 of an elevator device 81 which is operated by winding up a wire so as to move up and down and does not come in contact with the weighing table even during the descent of the cover.

The cleaner 23 comprises a table 91 whose level is in agreement with that of the weighing table of the electronic balance 22 and a suction port 92 fitted to the table 91 and connected to a suction device 29b. A plurality of indentatations 93 are formed around the suction port 92. The indentatations 93 serve as an air-path which communicates the inside to the outside of the constant volume receiver 6 when laying the receiver 6 upside down on the suction port 92. A cover 86 is positioned above the table 91. The cover 86 is a cylindrical container which is opened at the lower portion thereof and whose upper face has a plurality of venting holes. The cover 86 is fitted to the crossarm 82 of the elevator device 81 and is thus capable of moving up and down and is designed in such a manner that it can cover a region wider than the area of the table 91 on which the indentatations 93 are formed, when it is in the descent condition. The hopper 24 for disposing the used powdery sample is connected to the suction device 29b.

Figure 5:
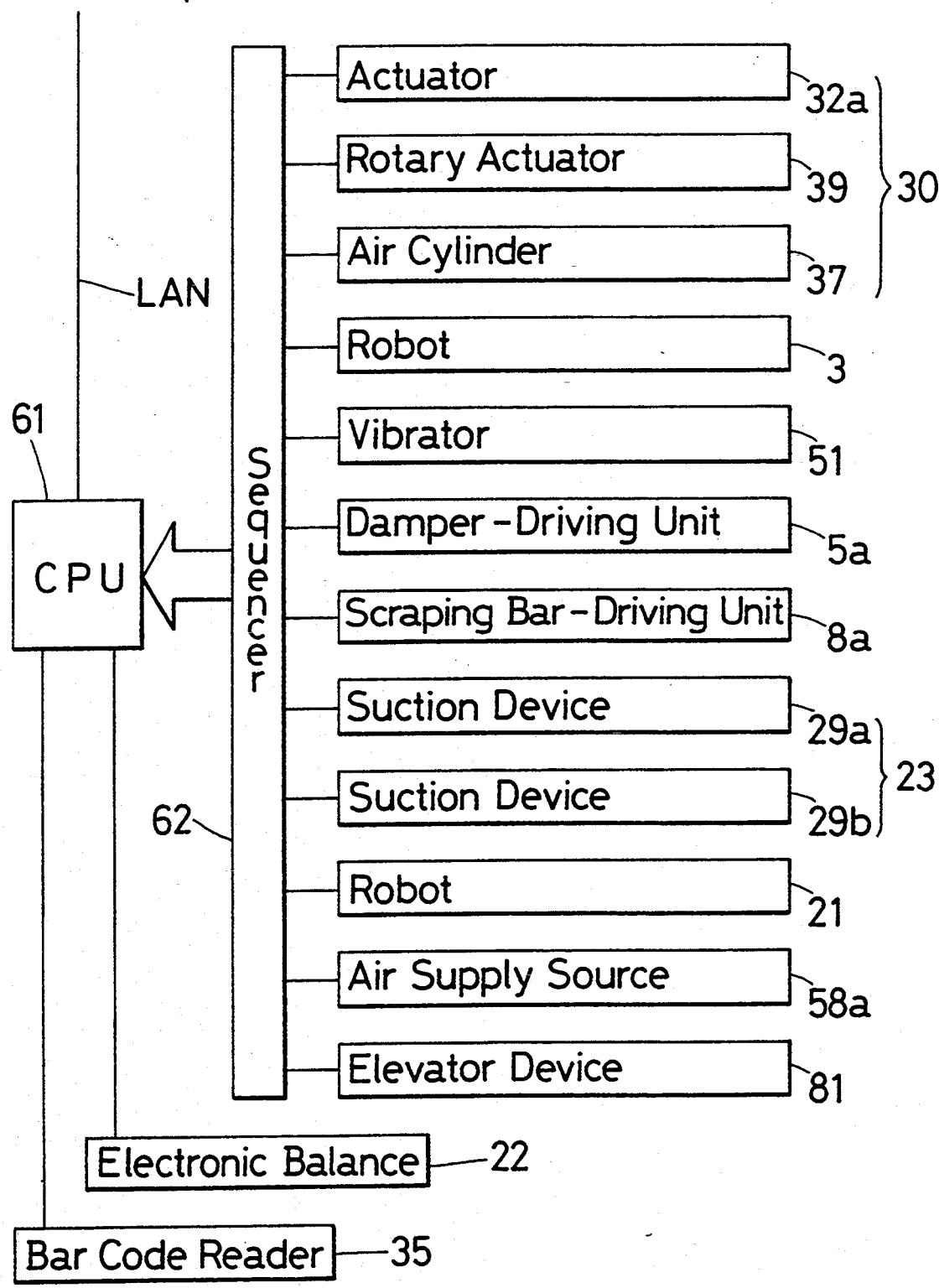
FIG. 5 is a control block circuit diagram for use in the embodiment of the apparatus for automatically determining the bulk specific gravity of a powdery sample shown in FIG. 1.

In the foregoing apparatus, there are connected, as shown in FIG. 5, the actuator 32a of the conveying device 30, the air cylinder 37, the rotary actuator 39, the sample container-conveying robot 3, the vibrator 51, the damper-driving unit 5a, the scraping bar-driving unit 8a, the suction devices 29a and 29b of the cleaner 23, the constant volume receiver-conveying robot 21, the air supply source 58a and elevator device 81 to a sequencer 62 which is in turn connected to an arithmetic and control unit 61 (a central processing unit: CPU). Moreover, the bar code reader 35 and the electronic balance 22 are connected to the arithmetic and control unit 61 and the arithmetic and control unit 61 is connected to a host computer through a local area network (LAN).

Figure 7A:
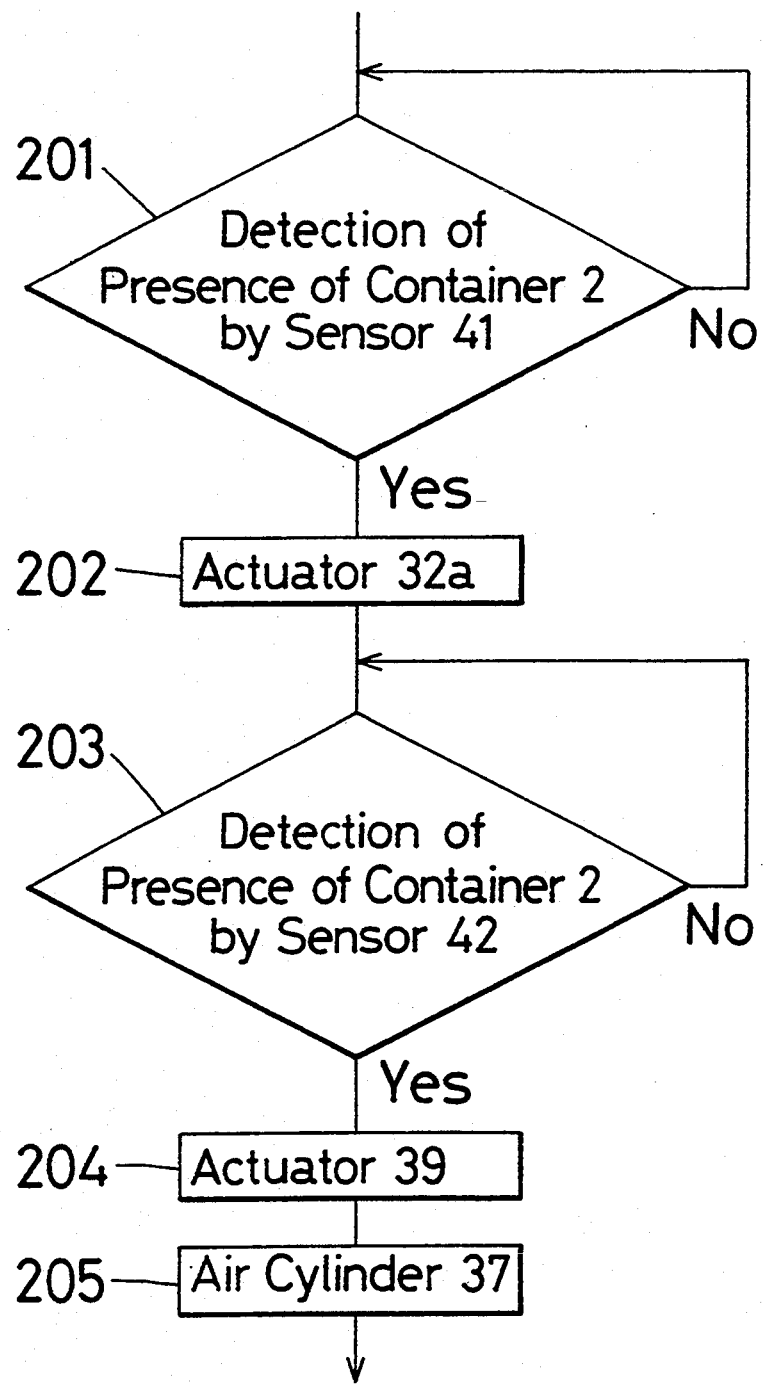
Figure 7C:
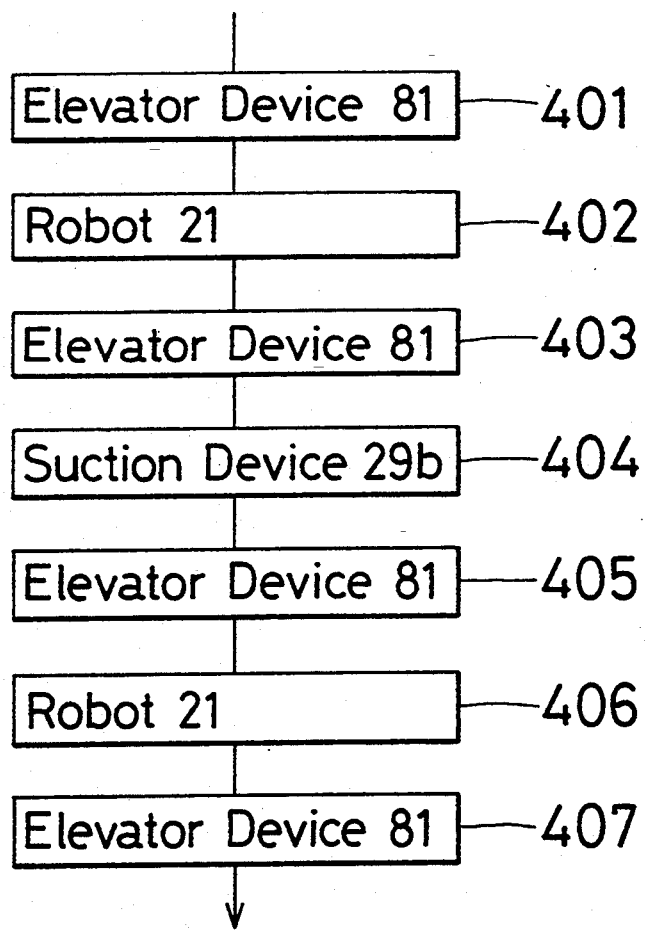

The apparatus for automatically determining the bulk specific gravity of a powdery product according to the present invention is in general operated as follows. The overall control of the apparatus is performed in accordance with the program incorporated into the arithmetic and control unit 61 (CPU), while the function of each device is controlled according to the control program incorporated into the sequencer 62. The function of the apparatus will hereunder be detailed with reference to the program chart incorporated into the arithmetic and control unit 61 and the control program chart incorporated into the sequencer 62 shown as a subroutine A (FIG. 7A), a subroutine B (FIG. 7B) and a subroutine C (FIG. 7C) for the program chart of the arithmetic and control unit 61.

An amount (120 cc each) of a powdery sample 1 is weighed out and introduced into a sample container 2. A label carrying a bar code 2a is attached to the side face of the sample container 2, the bar code 2a carrying coded data including the production lot number and the inspection number of the sample and the conditions for the inspection thereof. A plurality of the sample containers 2 are placed on a roller conveyor 31 and transferred to a desired position while they are aligned in a single line between a pair of guide rails 31a.

After confirming whether the apparatus is in its reset state or not, only one of the sample containers 2 is put on a turn table 34 by the action of a conveying device 30 which is operated in accordance with the instructions outputted from the arithmetic and control unit 61 which is inputted to the device 30 through the subroutine A (shown in FIG. 7A) for the sequencer 62 in the step 101 shown in FIG. 6. After a container sensor 41 detects or confirms the presence of the sample container 2 (step 201), an actuator 32a is put in operation (step 202) so that a stopper 32 temporarily retrocedes for permitting the passage of the forefront sample container 2. Then the sample container 2 is transferred, by the action of the roller conveyor 31, to a conveying bar 33 which stays at its home position. The second sample container 2 and those subsequent thereto are pressed against the stopper 32 and maintain their stand-by conditions. After a container sensor 42 detects or confirms whether the sample container 2 is transferred to the conveying bar 33 or not (step 203), a rotary actuator 39 is put in operation to ascend the conveying bar 33 (step 204) and the forefront sample container 2 is transferred to the end of the roller conveyor 31. Then the conveying bar 33 is returned to its horizontal state and an air cylinder 37 is put in operation to thus push the sample container 2 to the turn table 34 (step 205). After completion of this operation, the air cylinder 37 is temporarily returned to its original position.

A bar code reader 35 reads the bar code 2a in accordance with the instructions outputted from the arithmetic and control unit 61 in the step 102. The bar code reader 35 can scan over the bar code 2a to read it while rotating the sample container 2 on the turn table 34 by putting a motor 38 in operation. The bar code reader 35 then decodes the coded data including the production lot number, the inspection number and the conditions for the inspection of the powdery sample and forwards these data to the arithmetic and control unit 61.

The air cylinder is again put in operation (step 301) according to the instructions outputted from the arithmetic and control unit 61 which is inputted to the air cylinder 37 through the subroutine B (shown in FIG. 7B) for the sequencer 62 in the step 103, the conveying bar 33 pushes the sample container 2 on the turn table 34 (indicated by two-dot chain line in FIG. 2) to transfer the container to a conveyor table 36 and then the conveying bar 33 is returned to its home position. A sample container-conveying robot 3, which has been in its home position, holds the sample container 2, ascends and rotates to transfer the container 2 to a position above a funnel 4 provided with a damper (step 302). As seen from FIG. 8, the tip of the arm rotates to turn the sample container 2 upside down and to thus drop the powdery sample 1 present in the container 2 into the funnel 4 provided with a damper which stores the powdery sample therein. When a damper-driving unit 5a is then put in operation (step 303), the damper 5 is opened and the powdery sample 1 is accordingly dropped into a constant volume receiver 6 present on a pedestal 9 in a heaped-up condition. After a sample-detection sensor 7 detects or confirms whether the powdery sample is completely dropped from the funnel 4 at this stage (step 304), a scraping bar-driving unit 8a is put in operation (step 305) so that a scraping bar 8 slides on the upper face of the constant volume receiver 6. Thus, the excess powdery sample in the receiver 6 heaped with the powdery sample is dropped on the pedestal 9, passes through through holes 9b and is received by and stored in a hopper 11 for receiving the excess powdery sample. The excess powdery sample stored in the hopper 11 is aspirated through a suction device 29a (step 306). Then a constant volume receiver-conveying robot 21 holds the receiver 6 and transfers it to an electronic balance 22 (step 307) and thereafter the robot 21 is returned to its original position (home position). When putting an elevator device 81 in operation (step 308), a windbreak cover 85, which has been in its home position, descends (see FIG. 8) to thus prevent the shaking of the balance due to the wind. At this stage, the weight of the constant volume receiver 6 containing the powdery sample 1 is determined by the electronic balance 22. The damper-driving unit 5a is operated simultaneously with the initiation of the weight-determination by the electronic balance 22 to open the damper 5 (step 309). Air is injected through an air tube 58 when an air supply source 58a is put in operation (step 310) and the funnel 4 provided with a damper is vibrated by the action of a vibrating bar 51a and a knocker 51b when a vibrator 51 is operated (step 311). Thus, the powdery sample remaining in or adhered to the funnel 4 can be removed. Thereafter, the damper 5 is closed by operating the damper-driving unit 5a.

After completion of this operation, the weight of the constant volume receiver 6 (the sum of the weight of the powdery sample 1 and the tare weight of the receiver 6) is determined by the electronic balance 22 in accordance with the instructions outputted from the arithmetic and control unit 61 and the data thus obtained is forwarded to the arithmetic and control unit 61 in the step 104.

In the step 105, the elevator device 81 is put in operation according to the instructions outputted from the arithmetic and control unit 61 which is inputted to the device through the subroutine C (see FIG. 7C) for the sequencer 62 (step 401) to make the windbreak cover 85 ascend and to thus return the cover 85 to its home position. Thereafter, in the step 402, the constant volume receiver-conveying robot 21, which has been in the stand-by condition in the foregoing step 308, is put in operation to hold the constant volume receiver 6 on the electronic balance 22, transfer the receiver to the hopper 24, turn it upside down for the removal of the weighed powdery sample present therein, then transfer the vacant receiver 6 to a position above a cleaner 23 and put the receiver 6, which is turned upside down, on an air suction opening 92. The elevator device 81 is put in operation at this stage (step 403) to make a cover 86 descend for covering the constant volume receiver 6. When a suction device 29b is put in operation (step 404), the air flows into the constant volume receiver 6, along the path indicated by an arrow, through venting holes formed on the upper face of the cover 86 and indentations 93 formed on a table 91 and thus the powdery sample adhered to the inner wall of the receiver 6 is removed. At this stage, the disposed powdery sample stored in the hopper 24 is simultaneously aspirated by the suction device 29b. Then the elevator device 81 is put in operation in the step 405 to make the cover 86 ascend. In the step 406, the receiver-conveying robot 21 holds the vacant and cleaned constant volume receiver 6, returns the receiver to the electronic balance 22 and then retrocedes. Moreover, the elevator device 81 is put in operation to make the windbreak cover 85 descend (step 407).

After completion of this operation, the weight of the vacant constant volume receiver 6 is determined by the electronic balance 22 in accordance with the instructions outputted from the arithmetic and control unit 61 in the step 106 and the result (the tare weight of the receiver 6) is transferred to the arithmetic and control unit 61.

In the step 107, the elevator device 81 is put in operation through the instructions outputted from the arithmetic and control unit 61 which is inputted to the device through a subroutine D (the diagramatic description of each step thereof is herein omitted) for the sequencer 62 to make the windbreak cover 85 ascend. Then the constant volume receiver-conveying robot 21, which has retroceded in the foregoing step 407, is operated to hold the receiver 6 on the electronic balance 22, returns it to the pedestal 9 and then the robot 21 is returned to its home position.

On the other hand, the arithmetic and control unit 61 calculates, in the step 108, the bulk specific gravity (B.S.G.) of the powdery sample 1 on the basis of the following relation:

$$B.S.G. = [(\text{weight obtained in Step 104}) - (\text{weight obtained in Step 106})]/(\text{volume of the receiver 6})$$

In the step 108, the calculated data of the bulk specific gravities are transferred to the host computer through the LAN together with the production lot number, the inspection number and the conditions for the inspection which have been transferred to and stored in the arithmetic and control unit 61. These data can be outputted through a display device or a printer (not shown) connected to the arithmetic and control device 61.

In the foregoing step 103, i.e., the step 302 of the subroutine B, the sample container-conveying robot 3 holds the sample container 2 and turns the container upside down to drop the powdery sample 1 included in the sample container 2 into the funnel 4. Then the sample container-conveying robot 3 is put in operation in accordance with a subroutine E (the diagramatic description of each step thereof is herein omitted) for the sequencer 62 in the step 110 and is rotated towards the rear side of the device as shown in FIG. 2 to dispose the vacant sample container 2 through a container-disposing port 53. After the disposal of the vacant container 2, the sample container-conveying robot 3 returns to its stand-by position (home position) above the conveyor table 36.

After the completion of the foregoing series of operation steps 101 to 110, the apparatus returns to its reset state.

Incidentally, it is also possible, in the foregoing apparatus, to detect the initiation and termination of the dropping of the powdery sample by the powdery sample sensor 7 and to determine flow properties of the powdery sample 1 on the basis of the time required for the complete dropping of the sample, the shape of the funnel 4 provided with a damper and the amount of the powdery sample dropped through the funnel 4 (the amount of the powdery sample contained in the sample container 2), the determination of the flow properties being performed by the arithmetic and control unit 61.

Figure 3:
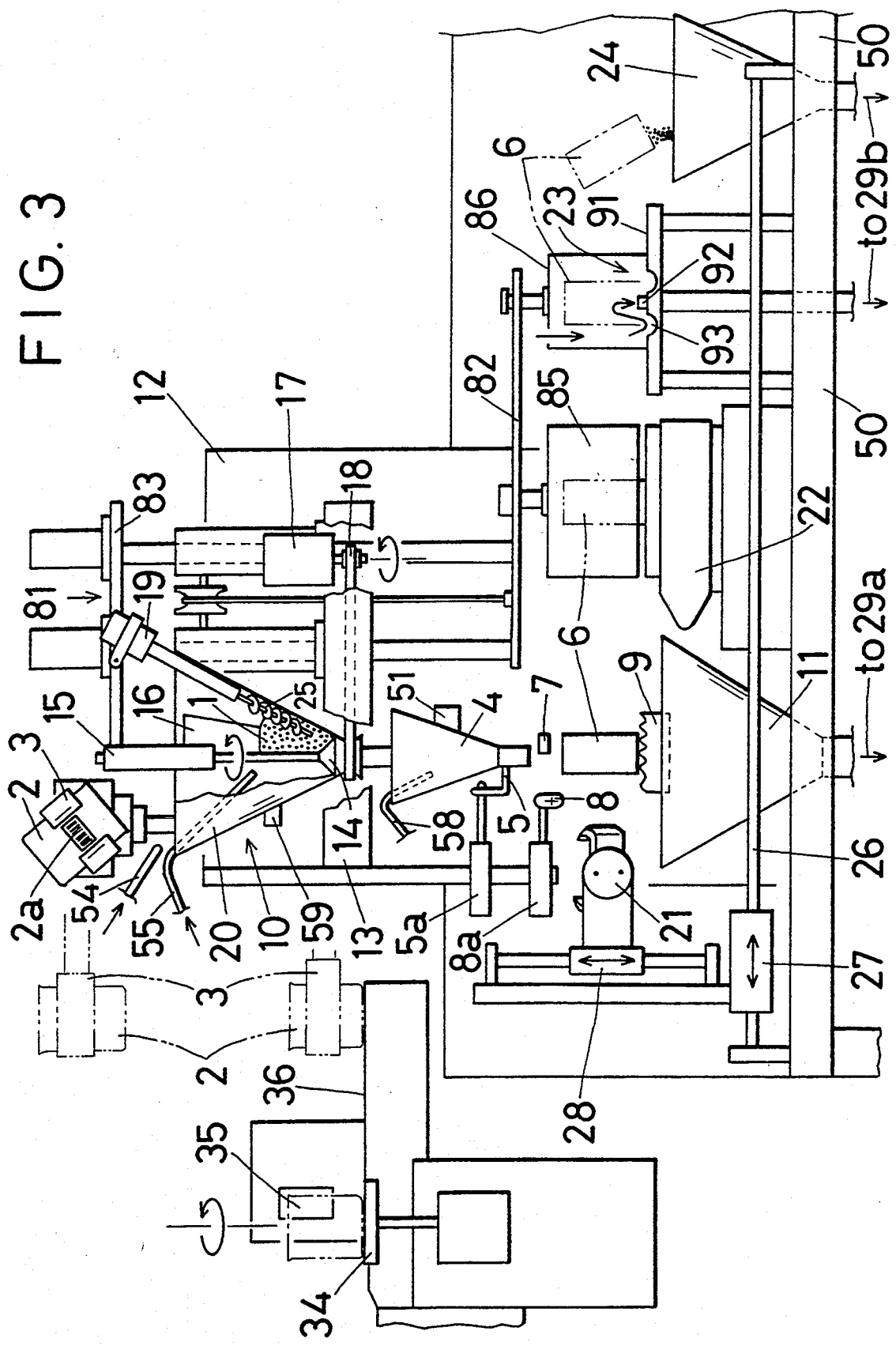
FIG. 3 is an enlarged elevational view showing the principal parts of the embodiment of the apparatus for automatically determining the bulk specific gravity of a powdery sample shown in FIG. 1.

FIG. 3 is an elevational view of principal parts of another embodiment of the apparatus for automatically determining the bulk specific gravity of a powdery product according to the present Invention. The apparatus for automatically determining the bulk specific gravity of a powdery product according to this embodiment comprises, in addition to the components of the apparatus already detailed above, a static charge eliminator 10 arranged at a position above the funnel 4 provided with a damper shown in FIG. 1, i.e., the position where a powdery sample 1 discharged from a sample container 2 by the action of a sample container-conveying robot 3 should be received.

The static charge eliminator 10 is a funnel 20 supported by an axis so that the outer wall thereof can be rotated and it is connected to a motor 17 as a driving unit through a belt 18. A bottom cover 14 capable of being opened and closed comes in close contact with the inner wall of a discharge port of the funnel 20. The axis of the bottom cover 14 is rotatably fitted in a sleeve 15 and the sleeve 15 is fitted to a crossarm 83 (see FIG. 2) of an elevator device 81 which is operated by winding up a wire. Moreover, a driving motor 19 for a screw agitator 25 is also fitted to the crossarm 83 and the screw agitator 25 is inserted into the funnel 20. The inclined inner wall of the funnel 20 is approximately parallel to the rotational axis of the screw agitator 25 and the funnel 20 is rotated in the direction opposite to the revolutionary direction of the screw agitator 25. In addition, a baffle plate 16 is firmly fitted to the sleeve 15. Therefore, the funnel 20 is rotated and the bottom cover 14 is likewise rotated due to frictional force when the motor 17 is rotated, but the sleeve 15 and the baffle plate 16 are not rotated. A vibrator 59 is fitted to the rear side of the funnel 20. Moreover, the tip of a static charge-eliminating solution supply tube 54, which is connected to a supply source 54a for the static charge-eliminating solution (see FIG. 9) is inwardly introduced into the funnel 20. In addition, an air tube 55 is also introduced into the funnel 20. The air tube 55 is connected to an air supply source 55a (see FIG. 9).

Figure 9:
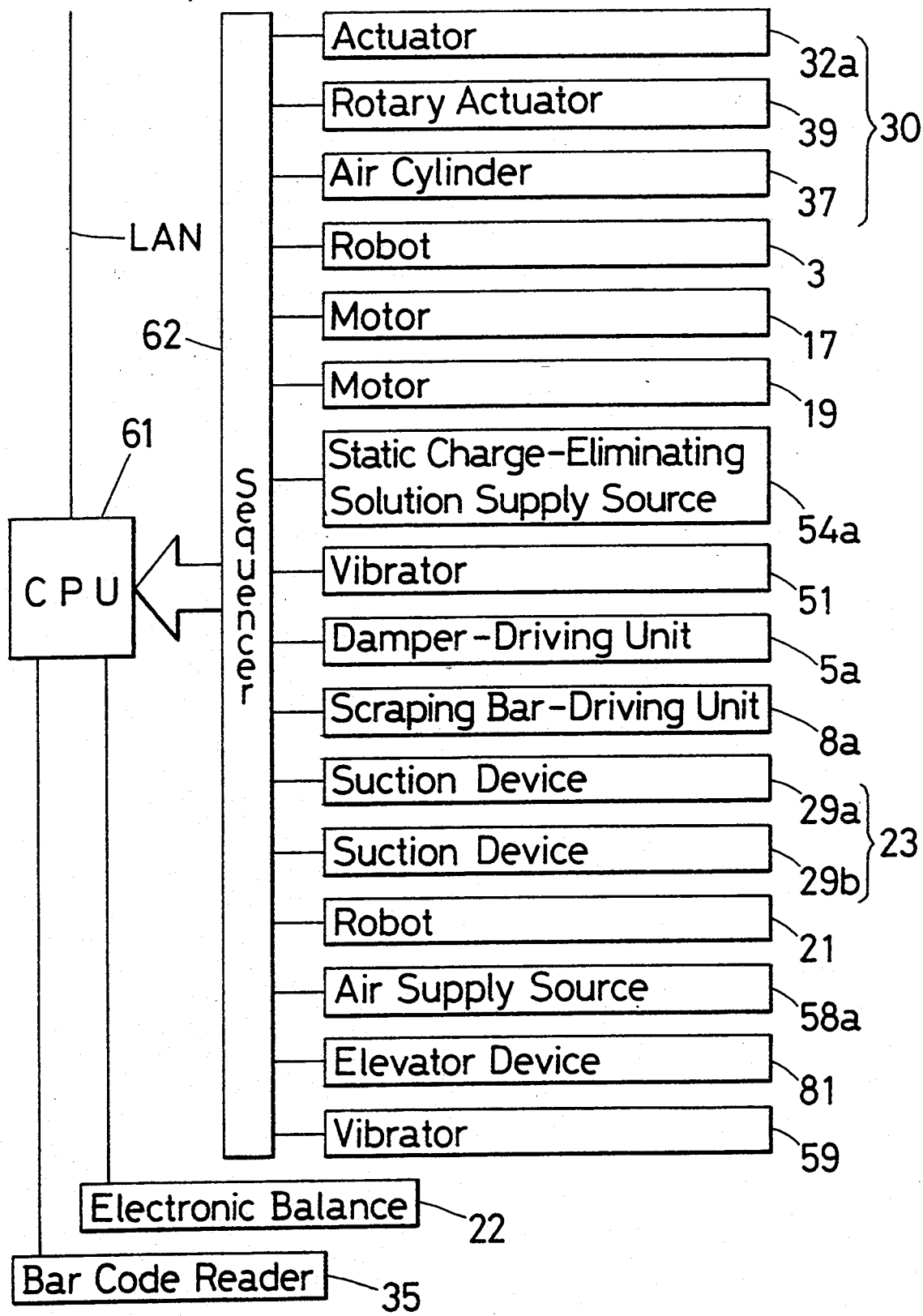
FIG. 9 is a control block circuit diagram for use in the embodiment of the apparatus for automatically determining the bulk specific gravity of a powdery sample shown in FIG. 8.

In the foregoing apparatus as shown in FIG. 9: an actuator 32a, an air cylinder 37 and a rotary actuator 39 of a conveying device 30; a sample container-conveying robot 3; a motor 17 for rotating the funnel 20; a driving motor 19 for a screw agitator 25; a supply source 54a for a static charge-eliminating solution; an elevator device 81; a vibrator 51; a damper-driving unit 5a; a scraping bar-driving unit 8a; suction devices 29a and 29b for a cleaner 23; a constant volume receiver-conveying robot 21; an air supply source 58a, and a vibrator 59 are connected to a sequencer 62, which is connected to a control unit 61 (central processing unit: CPU).

The apparatus for automatically determining the bulk specific gravity of a powdery product according to this embodiment, which is provided with a static charge eliminator is in general operated as follows. The overall control of the apparatus is performed in accordance with the program incorporated into the arithmetic and control unit 61 (CPU), while the function of each individual device is controlled according to the control program incorporated into the sequencer 62. The program chart for the arithmetic and control unit 61 shown in FIG. 9 is identical to that shown in FIG. 6 which has already been explained and, therefore, the details thereof is herein omitted for simplicity. Moreover, subroutines A and C are likewise identical to those shown in FIGS. 7A and 7C respectively and detailed explanation thereof is also omitted. On the other hand, the subroutine B shown in FIG. 10 differs from that shown in FIG. 7B and will hereunder be explained.

In the step 103 shown in FIG. 6, the apparatus is operated in accordance with the subroutine B for sequencer 62 shown in FIG. 10 through the instructions outputted from the arithmetic and control unit 61. More specifically, the air cylinder 37 is again put in operation (step 301), the conveying bar 33 correspondingly pushes the sample container 2 present on the turn table 34 to transfer the container 2 to the conveyor table 36 and then the conveying bar 33 returns to its home position. In the step 302, the sample container-conveying robot 3, which stays at its home position, holds the sample container 2, and rotates and transfers the sample container 2 to a position above the funnel 20. As seen from FIG. 3, the tip of the arm of the robot 3 is rotated to turn the sample container 2 upside down and to thus drop the powdery sample 1 into the funnel 20 in which the powdery sample is stored.

When the motor 17 is started at this stage (step 313), the funnel 20 is rotated and the bottom cover 14 capable of being opened and closed also rotates due to the frictional force applied thereto, but the baffle plate 16 does not rotate. When the motor 19 is started (step 314), the screw agitator 25 starts its rotational motion. If the the static charge-eliminating solution supply source 54a is put in operation (step 315), a static charge-eliminating solution is introduced into the funnel 20 through the tube 54 and is admixed with the powdery sample 1 stored therein. After properly admixing and stirring the mixture, the motors 17 and 19 are shut down. The funnel 20 is preferably rotated in the direction opposite to the rotational direction of the screw agitator 25 for the improvement of the mixing efficiency. The presence of the baffle plate 16, which does not rotate, permits uniform stirring of even a small amount the powdery sample 1. In this respect, the static charge-eliminating solution may be, for instance, a solution of a cationic surfactant in isopropyl alcohol. The use of an isopropyl alcohol solution permits rapid evaporation of the solvent from the powdery sample 1 and only the surfactant as an effective component of the static charge-eliminating solution remains on the powdery sample 1.

After completion of the static charge-eliminating operation which comprises adding a static charge-eliminating solution to the powdery sample 1 present in the funnel 20 and stirring and mixing them, the elevator device 81 is ascended in the step 316 to make the bottom cover 14 ascend and to thus drop the powdery sample 1 to the funnel 4 provided with a damper through the discharge port, the powdery sample 1 being stored in the funnel 4. The vibrator 59 is put in operation at this stage (step 317). Further, the air supply source 58a is operated (step 318), the air is injected through the air tube 55 to remove the powdery sample 1 adhered to the inner wall of the funnel 20, the bottom cover 14, the baffle plate 16 and the screw agitator 25, and the powdery sample 1 is dropped into the funnel 4 provided with a damper. Thereafter, the elevator device 81 is descended (step 319) to make the bottom cover 14 descend and to thus close the discharge port of the funnel 20.

When the damper-driving unit 5a is then put in operation (step 320), the damper 5 is opened and the powdery sample 1 is accordingly dropped into the constant volume receiver 6 present on the pedestal 9 in a heaped-up condition. After the sensor 7 detects or confirms if the powdery sample has been completely dropped from the funnel 4 at this stage (step 321), the scraping bar-driving unit 8a is put in operation (step 322) so that the scraping bar 8 slides on the upper face of the constant volume receiver 6. Thus, the excess powdery sample in the receiver 6 heaped-up with the sample is dropped on the pedestal 9, passes through the through holes 9b and is received by and stored in the hopper 11 for receiving the excess powdery sample. The excess powdery sample stored in the hopper 11 is aspirated through the suction device 29a (step 323). Then, the constant volume receiver-conveying robot 21 holds the receiver 6 and transfers it to the electronic balance 22 (step 324) and thereafter the robot 21 is returned to its original position (home position). Since the elevator device 81 is descended and the windbreak cover 85 is also descended in the foregoing step 319 (see FIG. 3), thus any shaking of the balance due to the wind can be prevented. At this stage, the weight of the constant volume receiver 6 containing the powdery sample 1 is determined by the electronic balance 22. On the other hand, air is injected through an air tube 58 by operating an air supply source 58a (step 325) to thus remove the powdery sample adhered to the inner wall of the funnel 4 whose damper is opened, the powdery sample thus removed being dropped into the hopper 11. Thereafter, the damper-driving unit 5a is operated to close the damper 5 (step 326).

After completion of this operation, the apparatus undergoes the operations programmed in the arithmetic and control unit 61 shown in FIG. 6. More specifically, the weight of the constant volume receiver 6 (the sum of the weight of the powdery sample 1 and the tare weight of the receiver 6) which is determined by the electronic balance 22 in accordance with the instructions outputted from the arithmetic and control unit 61 is forwarded to the arithmetic and control unit 61 in the step 104. The step 105 and those subsequent thereto are the same as those already explained above and, therefore, the explanation thereof is herein omitted for simplicity.

As has been explained above in detail, the apparatus for automatically determining the bulk specific gravity of a powdery product, equipped with a static charge eliminator, according to the present invention permits continuous automatic determination of bulk specific gravities of powdery products. The apparatus thus permits complete automation of the operations such as the supply of a powdery sample to the bulk specific gravity-determining apparatus, the determination of the volume and weight of the sample, the calculation of the bulk specific gravity thereof and the cleaning of a constant volume receiver and it is simply required for an operator to put the sample container containing a powdery sample on a conveying device. Thus, the apparatus is quite effective for the reduction of labor required for the inspection of powdery products. Moreover, the apparatus ensures reproducible and highly precise determination of the bulk specific gravity of the powdery sample since the measured values do not vary depending on operators and the determination is carried out after the elimination of electrostatic charges possibly present on the powdery sample. In addition, the apparatus according to the present invention is improved in such a manner that all of the factors which make the measured value inaccurate are eliminated and accordingly, permits highly precise measurement in this respect.

What is claimed is:

1. An apparatus for automatically determining the bulk specific gravity of a powdery product, comprising: a sample container-conveying robot which holds and transports a sample container filled with a powdery sample and turns the sample container upside down at a position having a predetermined height to discharge the powdery sample in the container; a static charge eliminator which receives the powdery sample discharged from the sample container by action of the sample container-conveying robot, stores the powdery sample, and admixes the powdery sample with a static charge-eliminating solution, said static charge eliminator comprising a first funnel which is provided with a bottom cover capable of being opened and closed, a rotational driving unit for rotationally driving the first funnel, a screw agitator inserted into the first funnel, and a static charge-eliminating solution supply source introduced into the first funnel; a second funnel which is provided with a damper, and which receives the powdery sample discharged from the static charge eliminator; a damper-driving unit for pulling out and pushing the damper; a sample sensor for detecting the sample dropped through the second funnel; a constant volume receiver for receiving the powdery sample dropped through the second funnel; a scraping bar which can slide on the upper face of the constant volume receiver; a scraping bar-driving unit for reciprocating the scraping bar; a constant volume receiver-conveying robot which holds and transports the constant volume receiver filled with the powdery sample and which can turn the receiver upside down; an electronic balance which receives the constant volume receiver transferred to the balance by the robot and determines a weight thereof; a cleaner for aspirating the weighed powdery sample; and control circuits for controlling the operations of the sample container-conveying robot, the damper-driving unit, the scraping bar-driving unit, the constant volume receiver-conveying robot, the electronic balance and the cleaner.

2. The apparatus for automatically determining the bulk specific gravity of a powdery product according to claim 1 wherein a bar code which stores at least a coded lot number or conditions for inspection of the sample is attached to the sample container filled with the powdery sample, the apparatus further comprises a bar code reader for reading the bar code and the control circuits output the sample lot number and the conditions for inspection read by the bar code reader and weighed values determined by the electronic balance.

3. The apparatus for automatically determining the bulk specific gravity of a powdery product according to claim 1 wherein the control circuits are connected to a host computer and the apparatus comprises a means for forwarding the weighed value outputted from the control circuit to the host computer together with the sample lot number and the conditions for inspection.

4. The apparatus for automatically determining the bulk specific gravity of a powdery product according to claim 1 further comprising a conveying device for conveying the sample container filled with the powdery sample to a position where the sample container-conveying robot holds the sample container.

5. The apparatus for automatically determining the bulk specific gravity of a powdery product according to claim 1, wherein the inclined inner wall of the first funnel is approximately parallel to the rotational axis of the screw agitator, and the first funnel is rotated in the direction opposite to a revolutionary direction of the screw agitator.

6. The apparatus for automatically determining the bulk specific gravity of a powdery product according to claim 1 wherein the powdery sample is a powdery vinyl chloride resin sample.

* * * * *